United States Patent [19]
Lin et al.

[11] Patent Number: 6,154,515
[45] Date of Patent: Nov. 28, 2000

[54] COMPUTERIZED TOMOGRAPHY RECONSTRUCTION USING SHADOW ZONE PATCHING

[75] Inventors: Wen-Tai Lin, Niskayuna; Peter Michael Edic, Albany, both of N.Y.

[73] Assignee: General Electric Company, Schenectady, N.Y.

[21] Appl. No.: 09/272,533

[22] Filed: Mar. 22, 1999

Related U.S. Application Data
[60] Provisional application No. 60/121,064, Feb. 22, 1999.

[51] Int. Cl.[7] ........................................................ A61B 6/03
[52] U.S. Cl. .................................. 378/4; 378/15; 378/901
[58] Field of Search ................................... 378/4, 15, 901

[56] References Cited

U.S. PATENT DOCUMENTS 5,278,884  1/1994  Eberhard et al. ............................ 378/4

OTHER PUBLICATIONS

"Practical Cone–Beam Algorithm," L. Feldkamp, L. Davis, J. Kress, J. Opt. Soc. Am., 1984, pp. 612–619.

"A Cone Beam Reconstruction Algorithm for the Circular Orbit and the Circle–and–Line Orbit," ASL Technical Report, General Electric Co., Hui Hu, Jan. 31, 1997, pp. 1–24.

"Efficient Cone–Beam Reconstruction System Using Circle–And–Line Orbit Data," Wen–Tai Lin, Mehmet Yavuz, Serial No. 09/253,706 (GE docket RD–26,008), filed Feb. 22, 1999.

*Primary Examiner*—David V. Bruce
*Attorney, Agent, or Firm*—Jill M. Breedlove; Douglas E. Stoner

[57] ABSTRACT

A source applies imaging energy that passes through an object being imaged and is then detected by a detector connected to a processor. A scanning trajectory includes first and second scan paths. The first scan path has a shadow zone where a complete image cannot be obtained from corresponding first scan path data. The second scan path provides data from the shadow zone. Partial images from the first scan path and the second scan path are Fourier transformed after which some data is removed prior to adding the Fourier data together. An inverse Fourier transform is then used to provide an overall image.

20 Claims, 3 Drawing Sheets

COMPUTERIZED TOMOGRAPHY RECONSTRUCTION USING SHADOW ZONE PATCHING

CROSS REFERENCE TO RELATED APPLICATIONS

This application claims the benefit of Provisional U.S. Patent application, Ser. No. (60/121,064), entitled, "Computerized Tomography Reconstruction Using Shadow Zone Patching," filed on Feb. 22, 1999, and assigned to the assignee of the present application.

This application is related to co-pending U.S. patent application Ser. No. 09/253,706, entitled, "Efficient Cone Beam Reconstruction System Using Circle-and-Line Orbit Data," filed on Feb. 22, 1999, assigned to the assignee of the present application, and herein incorporated by reference.

BACKGROUND OF THE INVENTION

This invention relates to X-ray imaging techniques, and, more particularly, to computerized tomography X-ray imaging using data combined from different scan paths.

Computerized tomography (CT) uses a source of imaging energy such as X-ray energy and a detector for detecting imaging energy that has passed through an object of interest, often a patient being imaged for medical purposes. Typically, a single point source is used with an area detector such as an X-ray detector array.

Relative movement between the source, object of interest, and detector is used to collect data for image reconstruction purposes.

The advent of area X-ray detectors permits measurement of a 2 dimensional data set for each source position, since the detector lies in a 2 dimensional plane. Therefore, it is possible to measure a 1+2=3 dimensional data set of line integrals of the object being imaged.

This dimensional count is encouraging for volumetric imaging such as CT because the imaged object lies in three spatial dimensions. More specifically, complete CT data for a family of parallel planes constitutes a 2+1=3 dimensional data set and completely determines the imaged object.

Unfortunately, cone beam data generated by a single point source does not permit such simple reconstruction. A single circular trajectory does not provide a complete data set for Radon reconstruction (i.e., apart from measurement and discretization errors). Therefore, various scan trajectories have been used.

Generally, the scan trajectories result from relative movement among the source, detector, and object being imaged. Usually, the source is moved in a path about the object to define the scan trajectory. The object being imaged is often a medical patient, but could also be an industrial part being imaged to locate possible defects. Regardless of whether the object being imaged is a patient or an industrial part, the scan trajectory may be defined at least partly by movement of the object relative to the source or relative to the detector.

It has been long known that exact three dimensional (3D) reconstruction of a scanned object requires that any plane intersecting the object must also intersect the scanning path. Therefore, a planar orbit such as the circular orbit with its inherent simplicity and rotational symmetry is not sufficient to provide exact 3D reconstruction.

In order to provide exact 3D reconstruction, scan trajectories use more than one scan path for imaging a given object. A scan trajectory often uses two scan paths, a circular scan path and a complementary scan path. A linear path orthogonal to the plane of the circular scan path is a common scan path used to complement the circular scan path. Another scan paths used to complement a first circular scan path is a second circular orbit tilted relative to the first circular orbit.

Such scan trajectories that provide complete cone beam data may present a number of problems. The imaging often requires highly sophisticated, time-consuming algorithms. Noise and artifacts often result from techniques using interpolation in Radon space.

BRIEF SUMMARY OF THE INVENTION

In an exemplary embodiment of the method of the invention, an object is imaged by applying imaging energy from a source to the object. Imaging energy that has passed through the object is detected by a detector. The object is scanned with the imaging energy in first and second scan paths such that the detector collects first path measured image data from the first scan path and second path measured image data from the second scan path. The first and second scan paths are geometrically distinct, meaning that the two scan paths are not defined by a single equation. The first scan path defines a shadow zone for which Radon data are not available from the first scan path, whereas the second scan path is sufficient to provide measured image data for at least the shadow zone and a near shadow zone. The shadow zone and near shadow zone together are an augmented shadow zone, the object having a complementary zone complementary to the augmented shadow zone. Fourier transforms are applied to the first and second reconstructed image data to respectively provide first and second Fourier transform data. Augmented shadow zone Fourier transform data is obtained from the second Fourier transform data. Complementary Fourier transform data is obtained by removing augmented shadow zone Fourier transform data from the first Fourier transform data. The augmented shadow zone Fourier transform data and the complementary Fourier transform data are combined to provide overall Fourier transform data. An inverse Fourier transform is applied to the overall Fourier transform data to provide overall image data. An image of the object is supplied based on the overall image data.

An exemplary embodiment of the system of the invention includes a source for applying imaging energy to an object. A detector detects imaging energy that has passed through the object. A positioner scans the object with the imaging energy such that the detector collects first path measured image data from a first scan path and second path measured image data from a second scan path. The first scan path defines a shadow zone for which Radon data are not available from the first scan path and the second scan path is sufficient to provide measured image data for at least the shadow zone and a near shadow zone. The shadow zone and near shadow zone together are an augmented shadow zone and the object has a complementary zone complementary to the augmented shadow zone. The first and second scan paths are geometrically distinct. A processor operably connected to the detector is operable to reconstruct first and second images corresponding respectively to first and second reconstructed image data from the respective first path measured image data and the second path measured image data. The processor applies Fourier transforms to the first and second reconstructed image data to respectively provide first and second Fourier transform data, the processor obtaining augmented shadow zone Fourier transform data from the second Fourier transform data and obtaining complementary Fourier transform data by removing augmented shadow zone Fourier transform data from the first Fourier transform data. The processor is further operable to combine the augmented shadow zone Fourier transform data and the complementary Fourier transform data to provide overall Fourier transform data. The processor is further operable to apply an inverse Fourier transform to the overall Fourier transform data to provide overall image data. An image supplier operably connected to the processor supplies an image of the object based on the overall image data.

DETAILED DESCRIPTION OF THE INVENTION

Figure 1:
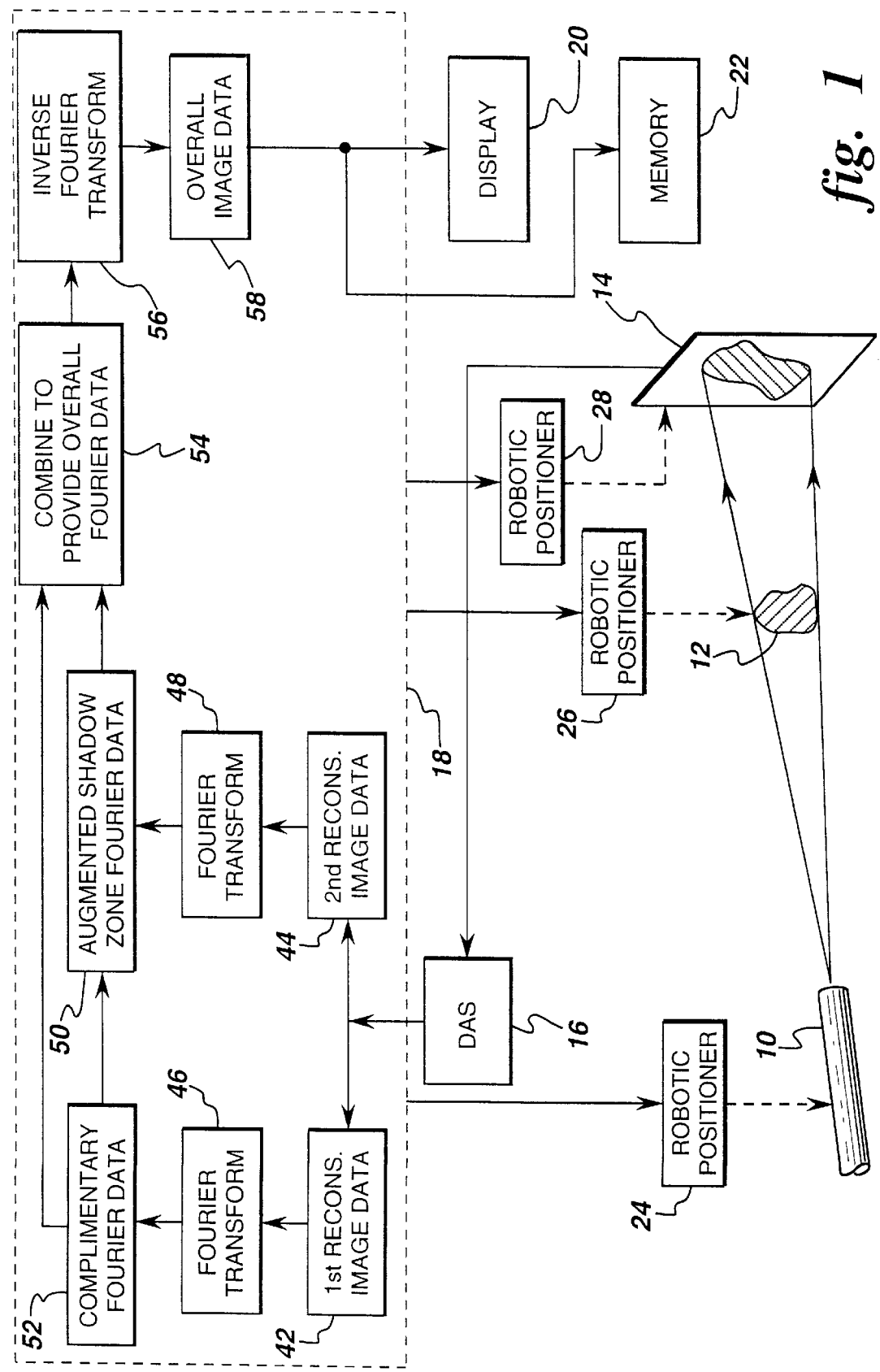
FIG. 1 is a block diagram of components of an imaging system and showing process steps within a processor.

Referring now to FIG. 1, imaging energy is applied by source 10 to object 12 and detected by detector 14. The source 10 typically comprises a cone beam X-ray source and the detector 14 typically comprises an area detector such as a two dimensional array detector having an array of individual detector elements (separate elements not shown). The object 12 typically comprises a patient (human or animal or tissue mass). Alternately, object 12 is an industrial part or other object being imaged using CT.

Cone beam energy that has passed through the object 12 is detected in detector 14 and converted to corresponding electrical signals and sent to a data acquisition unit 16 that registers the electrical signals. Unit 16 in turn sends cone beam data to a processor 18, which commonly comprises a computer programmed to perform various process steps. Various process steps performed within processor 18 are shown in simplified form in FIG. 1. Those steps will be discussed after a discussion of mathematics used in the present invention. At this stage, the processor reconstructs two sets of image data corresponding to two geometrically distinct scan paths such as a circular first scan path followed by an orthogonal linear second scan path or a circular first scan path followed by a circular second scan path tilted relative to the first circular scan path. The processor Fourier transforms the two sets, makes adjustments to the two Fourier transform sets, combines the two adjusted Fourier transform sets, inverse Fourier transforms the last two sets, and provides image data, which data is displayed in display 20 and stored in memory 22.

The scanning trajectory will be defined by relative movements of the source 10, object 12, and detector 14 respectively controlled by robotic positioners 24, 26, and 28. Each of the robotic positioners 24, 26, and 28 causes relative scanning movement among the source 10, object 12, and detector 14. The positioners 24, 26, and 28 are in turn controlled by processor 18 to realize a scan trajectories discussed below.

Figure 2:
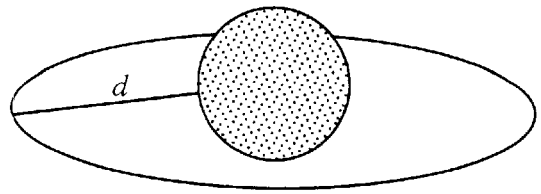
FIG. 2 is an illustration of a circular orbit around an object being imaged.

FIG. 2 will be used to explain basic concepts used by the present invention.

The invention provides exact 3D reconstruction, meaning it provides image reconstruction accurate other than measurement errors and discretization errors. Measurement errors may arise from, for example, from imprecision of the relative positioning of source and detector. Discretization errors can arise, for example, from basing measurements on the assumption that the source is at a plurality of discrete positions as it moves about its trajectory.

Figure 3:
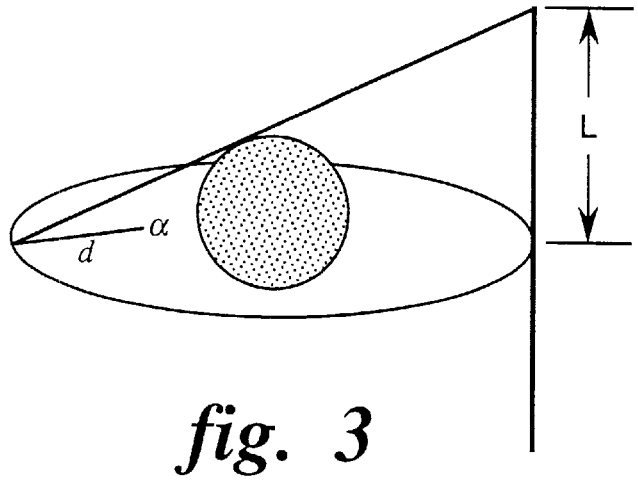
FIG. 3 an illustration of a scan trajectory having a circular orbit scan path around an object being imaged and a line scan path orthogonal to the plane of the circular orbit.

The geometry of a single circular orbit and a circle-and-line scanning trajectory are shown in FIGS. 2 and 3 respectively, where d is the radius of the circular orbit, R is the radius of the spherical functional support of the object and L is the half length of the linear orbit or path. It has been shown that as long as $L \geq 2dR(d^2-R^2)^{-\frac{1}{2}}$, the scanner satisfies the sufficient condition to provide exact reconstruction. In fact, any plane intersecting the object intersects the circle-and-line orbit 1, 2, or 3 times.

Figure 4:
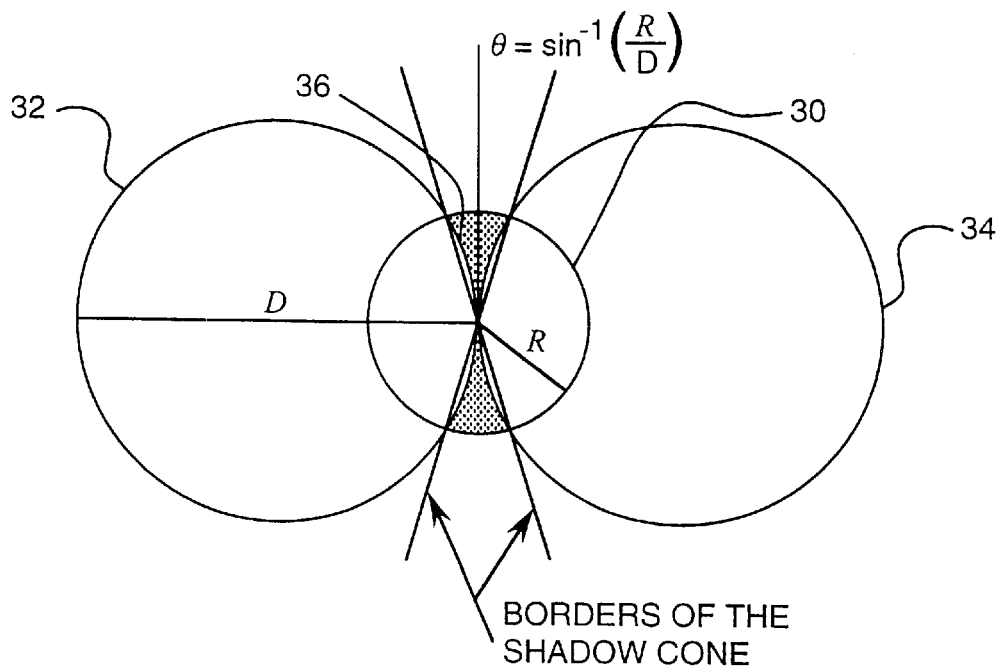
FIG. 4 a cross-sectional view of the circular orbit of FIG. 2.

A cross-section of FIG. 2 is shown in FIG. 4, where a shadow zone is defined. The shadow zone for which the circular orbit does not provide complete data for reconstruction is the shaded area in FIG. 4. This zone in the cross-section of FIG. 4 is the area within object circle 30 that is also outside of both circles 32 and 34 of diameter d.

The shadow zone is completely within a pair of cones 36 extending in opposite direction from the center of the object. The cone spans 2θ where $\theta=\sin^{-1}(R/D)$.

This cone region will be referred to as the shadow cone, or, more generally, the augmented shadow zone.

Figure 8:
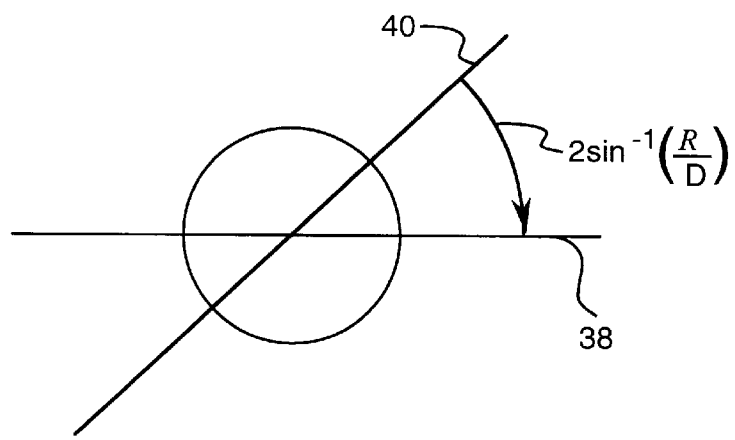
FIG. 8 is a simplified side view showing two circular orbits tilted relative to each other.

Based on the cross-sectional structure of FIG. 4, it is clear that when two identical circular orbits sharing the same center and with their planes of rotation forming an angle of at least 2 θ degrees, the shadow zone of each orbit would be fully complemented by its counterpart. Thus, a scan trajectory having a first circular orbit scan path 38 and a second circular orbit scan path 40 as shown in FIG. 8 with the indicated angle between them have non-overlapping shadow zones such that the two circular orbit complement each other.

It is less clear how a linear orbit as defined in FIG. 3 can complement the shadow zone of the circular orbit, but a technique providing such complementing is provided as discussed below.

A technique for reconstruction of image data from a line orbit can be done differently from the computationally demanding Hu line algorithm technique. From FIG. 3, it is clear that the X-ray source must have a cone angle of 2α to fully encompass the object (when the former is positioned in the middle of the linear orbit). A practical way of implementing the line-and-circle orbit would be to move and rotate the object by the following four steps: (1) hold the source and detector panel still, (2) translate the object from below the beam until it is lined up with source and the center of the detector panel, (3) make a 360 degrees of the object to fulfill the circular orbit, and (4) continue to move the object out of the cone beam.

Figure 5:
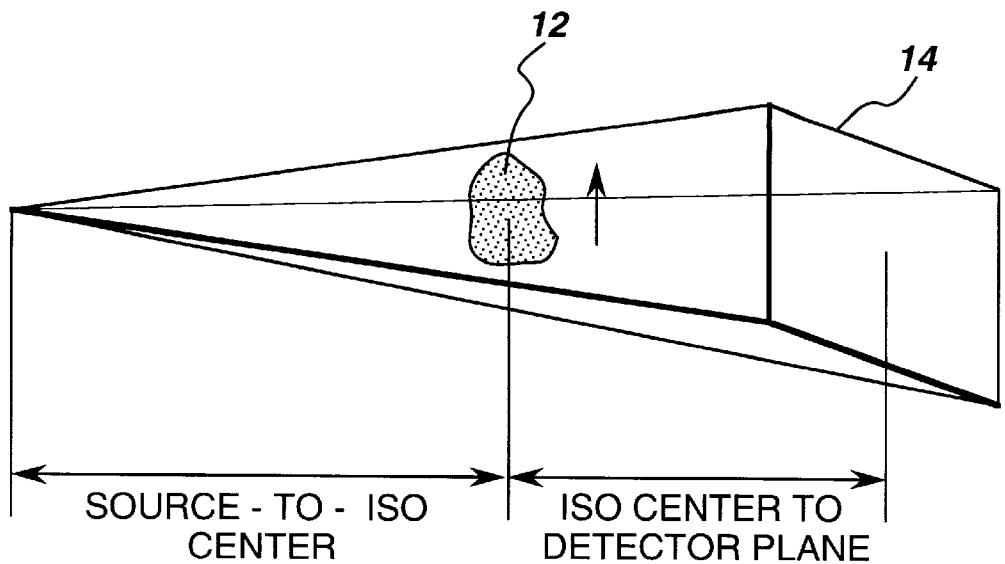
FIG. 5 is an illustration of an object being moved through a cone beam.
Figure 6:
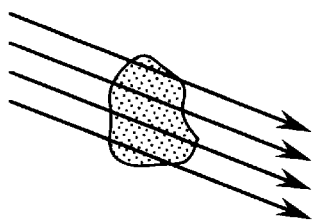
FIG. 6 is an illustration of the beam orientations collected from bottom rows of a detector plane from the movement of FIG. 5.
Figure 7:
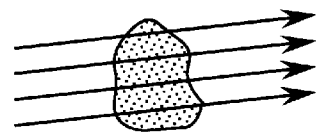
FIG. 7 is an illustration of the beam orientations collected from top rows of a detector plane from the movement of FIG. 5.

FIG. 5 shows that each detector element collects a set of parallel beams from the object's linear movement. The detector elements of the same column put together a sequence of parallel beams tilting from $-\alpha$ to $\alpha$; these column detectors intercept the same vertical slice of the object. Based on the central slice theorem, each reconstructed slice in its own 2D Fourier space could only recover a segment of the object's total frequency components. The two segments (or sectors) in frequency domain each subtends an angle of $2\alpha$ degrees.

The detector panel 14 consists of M rows by M columns of closely butted detectors and K snapshots (or projection views) have been taken when the object is engaged in the linear motion. Following the conventional backprojection procedures (or, using direct Fourier method for a fast algorithm), M slices of the object are independently reconstructed. Due to the cone beam structure, these M slices form a horn-shaped volume. A simple interpolation scheme converts the horn-shaped volume into a regular 3D grid array. The partially recovered object from the linear orbit or path can now be combined with the core image obtained from the circular orbit using the known Feldkamp's algorithm.

Turning now to the processing blocks within processor 18 of FIG. 1, $f_c(r)$ and $f_l(r)$ are the original images reconstructed from the circular and linear orbits via Feldkamp's algorithm and the backprojection procedure described above, respectively. The following steps describe how these two pieces of images from blocks 42 and 44 respectively can be combined:

1. Define a shadow cone in the Radon space with its angle subtending $2\theta$.
2. The shadow cone in Radon space is directly mapped into the 3D Fourier space, which appears to be the similar cone of angle $2\theta$ and with a finite support. Denote the shadow cone in 3D Fourier space as $F_c$.
3. Transform $f_c(r)$ and $f_l(r)$ into 3D Fourier space at blocks 46 and 48 respectively and denote the transformations as $F_c$ and $F_l$ respectively.
4. Obtain $F_{sc}$ (Fourier data for the shadow cone) from $F_l$ by deleting the non-shadow cone data within $F_l$ at block 50, while block 46 supplies $F_{ns}$ (Fourier data outside the shadow cone) by removing shadow cone data from $F_c$ at block 52.
5. The total or overall Fourier data is $F_t=F_{sc}+F_{ns}$ combined at block 54 and transformed at block 56 back to the image domain $f_t$ at block 58.

The finite grid resolution in both the image and Fourier spaces results in the shadow cone in $F_{ns}$ not necessarily being empty (before patching). To make a smooth transition between $F_{ns}$ and $F_{sc}$ an appropriate weighting function, w, is used to blend them. That is, $F_t=(1-w)F_{sc}+wF_{ns}$. Accordingly, $f_t$ is now a complete image with the redundancy error well taken care. This is done in the process of replacing the shadow zone with the shadow cone in Radon space. This is due to the fact that, out of the entire torus-shaped region where the valid Radon data reside, only the Radon data bordering the surface of the shadow zone have its planes of integral intercepting the circular orbit at one point, while the rest of the Radon data within the torus all have two intercepting points. However, this is no longer true after the shadow zone is replaced by the slightly larger shadow cone. That is, all the remaining Radon data have its planes of integral intercepting the circular orbit at two different points.

While the invention has been described with reference to a preferred embodiment, it will be understood by those skilled in the art that various changes may be made and equivalents may be substituted for elements thereof without departing from the scope of the invention. In addition, many modification may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of imaging an object comprising the steps of:
   applying imaging energy from a source to the object;
   detecting imaging energy that has passed through the object by use of a detector;
   scanning the object in first and second scan paths with the imaging energy such that the detector collects first path measured image data from the first scan path and second path measured image data from the second scan path, the first scan path defining a shadow zone for which Radon data are not available from the first scan path, the second scan path being sufficient to provide measured image data for at least the shadow zone and a near shadow zone, the shadow zone and near shadow zone together being an augmented shadow zone, the object having a complementary zone complementary to the augmented shadow zone, the first and second scan paths being geometrically distinct;
   reconstructing first and second images corresponding respectively to first and second reconstructed image data from the respective first path measured image data and the second path measured image data;
   applying Fourier transforms to the first and second reconstructed image data to respectively provide first and second Fourier transform data;
   obtaining augmented shadow zone Fourier transform data from the second Fourier transform data;
   obtaining complementary Fourier transform data by removing augmented shadow zone Fourier transform data from the first Fourier transform data;
   combining the augmented shadow zone Fourier transform data and the complementary Fourier transform data to provide overall Fourier transform data;
   applying an inverse Fourier transform to the overall Fourier transform data to provide overall image data; and
   supplying an image of the object based on the overall image data.

2. The method of claim 1 wherein the first scan path is an orbit in a plane and the second scan path extends outside the plane.

3. The method of claim 2 wherein the first scan path is a circular orbit and the second scan path is a line.

4. The method of claim 3 wherein the augmented shadow zone are two cones.

5. The method of claim 4 wherein the scanning step includes the substeps of: maintaining the source and the detector stationary relative to each other while moving the object relative to the source and detector in a line until the object is in the plane of the first scan path to provide a portion of the second scan path; then rotating the object relative to the source and the detector; and then maintaining the source and the detector stationary relative to each other while moving the object relative to the source and detector in a line to complete the second scan path.

6. The method of claim 4 wherein the combining of the augmented shadow zone Fourier transform data and the complementary Fourier transform data includes weighting the data to make a smooth transition between augmented shadow zone Fourier transform data and the complementary Fourier transform data.

7. The method of claim 1 wherein the combining of the augmented shadow zone Fourier transform data and the complementary Fourier transform data includes weighting the data to make a smooth transition between augmented shadow zone Fourier transform data and the complementary Fourier transform data.

8. The method of claim 1 wherein the first and second scan paths allow exact 3D reconstruction.

9. The method of claim 1 wherein the shadow zone is a region of the object functional support which is exterior to the torus and the augmented shadow zone are two cones.

10. The method of claim 1 wherein the first scan path is an orbit in a plane and the second scan path is a line normal to the plane.

11. A system for imaging an object comprising:

a source of imaging energy;

a detector;

a positioner scanning the object with the imaging energy such that the detector collects first path measured image data from a first scan path and second path measured image data from a second scan path, the first scan path defining a shadow zone for which Radon data are not available from the first scan path, the second scan path being sufficient to provide measured image data for at least the shadow zone and a near shadow zone, the shadow zone and near shadow zone together being an augmented shadow zone, the object having a complementary zone complementary to the augmented shadow zone, the first and second scan paths are geometrically distinct;

a processor operably connected to the detector and operable to reconstruct first and second images corresponding respectively to first and second reconstructed image data from the respective first path measured image data and the second path measured image data, the processor operable to apply Fourier transforms to the first and second reconstructed image data to respectively provide first and second Fourier transform data, the processor obtaining augmented shadow zone Fourier transform data from the second Fourier transform data and obtaining complementary Fourier transform data by removing augmented shadow zone Fourier transform data from the first Fourier transform data, the processor operable to combine the augmented shadow zone Fourier transform data and the complementary Fourier transform data to provide overall Fourier transform data, the processor further operable to apply an inverse Fourier transform to the overall Fourier transform data to provide overall image data; and an image supplier operably connected to the processor and supplying an image of the object based on the overall image data.

12. The system for imaging an object of claim 11 wherein the positioner is operable to provide an orbit in a plane as the first scan path and to provide the second scan path extending outside the plane.

13. The system for imaging an object of claim 12 wherein the positioner is operable to provide that the first scan path is a circular orbit and the second scan path is a line.

14. The system for imaging an object of claim 13 wherein the augmented shadow zone are two cones.

15. The system for imaging an object of claim 14 wherein the positioner is operable to: maintain the source and the detector stationary relative to each other while moving the object relative to the source and detector in a line until the object is in the plane of the first scan path to provide a portion of the second scan path; then rotate the object relative to the source and the detector; and then maintain the source and the detector stationary relative to each other while moving the object relative to the source and detector in a line to complete the second scan path.

16. The system for imaging an object of claim 14 wherein the processor combines the augmented shadow zone Fourier transform data and the complementary Fourier transform data with weighting of the data to provide a smooth transition between augmented shadow zone Fourier transform data and the complementary Fourier transform data.

17. The system for imaging an object of claim 11 wherein the processor combines the augmented shadow zone Fourier transform data and the complementary Fourier transform data with weighting of the data to provide a smooth transition between augmented shadow zone Fourier transform data and the complementary Fourier transform data.

18. The system for imaging an object of claim 11 wherein the positioner provides first and second scan paths which allow exact 3D reconstruction.

19. The system for imaging an object of claim 11 wherein the augmented shadow zone are two cones.

20. The system for imaging an object of claim 11 wherein the positioner provides that the first scan path is an orbit in a plane and the second scan path is a line normal to the plane.

* * * * *